(12) United States Patent
Al-Otaibi et al.

(10) Patent No.: US 12,072,328 B2
(45) Date of Patent: Aug. 27, 2024

(54) DYNAMIC IN-SITU MEASUREMENT OF CALCIUM ION CONCENTRATION IN POROUS MEDIA EXPERIMENTS

(71) Applicant: SAUDI ARABIAN OIL COMPANY, Dhahran (SA)

(72) Inventors: Mohammed Badri Al-Otaibi, Dhahran (SA); Dong Kyu Cha, Dhahran (SA)

(73) Assignee: SAUDI ARABIAN OIL COMPANY, Dhahran (SA)

(*) Notice: Subject to any disclaimer, the term of this patent is extended or adjusted under 35 U.S.C. 154(b) by 42 days.

(21) Appl. No.: 17/643,264

(22) Filed: Dec. 8, 2021

(65) Prior Publication Data

US 2023/0176029 A1 Jun. 8, 2023

(51) Int. Cl.
*G01N 33/24* (2006.01)
*G01N 27/30* (2006.01)
*G01N 27/416* (2006.01)

(52) U.S. Cl.
CPC ........... *G01N 33/24* (2013.01); *G01N 27/308* (2013.01); *G01N 27/4161* (2013.01)

(58) Field of Classification Search
CPC ... G01N 33/24; G01N 27/308; G01N 27/4161
See application file for complete search history.

(56) References Cited

U.S. PATENT DOCUMENTS 4,074,755 A 2/1978 Hill et al.
4,758,325 A * 7/1988 Kanno ............... G01N 27/3335
  204/411
6,068,054 A 5/2000 Bragg
(Continued)

FOREIGN PATENT DOCUMENTS

CN 102507696 A * 6/2012
CN 209745965 U * 12/2019
(Continued)

OTHER PUBLICATIONS

Wever et al., Comblike polyacrylamides as flooding agent in enhanced oil recovery, I&EC Research, 2013, 52, 16352-16363 (Year: 2013).*
Assem et al., Location and magnitude of formation damage due to iron precipitation during acidizing carbonate rocks, Journal of Petroleum Science and Engineering, 2019, 179, 337-354 (Year: 2019).*

(Continued)

*Primary Examiner* — Luan V Van
*Assistant Examiner* — Shizhi Qian

(57) ABSTRACT

Provided is a coreflood apparatus that comprises a housing, an inlet, an outlet, and two chambers positioned within the housing that are configured to retain porous media. The apparatus includes a partition coupled to an inner surface of the housing between the two chambers and a sensor mounting location. Provided is a method of introducing a fluid into the coreflood apparatus and allowing fluid to pass through chambers in the apparatus having a sensor mounting location there between. Further provided is a coreflood system comprising a coreflood apparatus, a calcium ion sensor, and a data processing device. Provided is a method of introducing fluid into the coreflood system and allowing fluid to pass through chambers in the system having a calcium ion sensor there between. The method further comprises detecting calcium ions in the fluid and determining calcium ion concentration data.

25 Claims, 5 Drawing Sheets

(56) References Cited

U.S. PATENT DOCUMENTS

| | | |
|---|---|---|
| 2005/0170975 A1 | 8/2005 | Collins |
| 2008/0236845 A1 | 10/2008 | Morrow et al. |
| 2009/0275488 A1 | 11/2009 | Zamora et al. |
| 2012/0018160 A1 | 1/2012 | Al-Yousef et al. |
| 2012/0125603 A1 | 5/2012 | Willingham et al. |
| 2013/0125630 A1* | 5/2013 | Collins .................... G01N 1/00 73/64.56 |
| 2016/0109334 A1 | 4/2016 | Collins et al. |
| 2019/0233713 A1 | 8/2019 | Chawathe et al. |
| 2019/0257182 A1 | 8/2019 | Couves et al. |
| 2020/0201658 A1 | 6/2020 | Su et al. |
| 2021/0238998 A1* | 8/2021 | Elsayed .................... G01V 3/32 |

FOREIGN PATENT DOCUMENTS

| | | | |
|---|---|---|---|
| CN | 112924618 A | * 6/2021 | |
| WO | WO-2020252801 A1 | * 12/2020 | ............ E21B 49/00 |

OTHER PUBLICATIONS

Ping et al., English translation of CN-102507696-A, 2012 (Year: 2012).*

Abhishek et al., Effect of silica nanoparticles on fluid/rock interactions during low salinity water flooding of chalk reservoirs, Applied Sciences, 2018, 8, 1093 (Year: 2018).*

Druetta et al., Influence of physical and rheological properties of sweeping fluids on residual oil saturation at the micro- and macroscale, Journal of Non-Newtonian fluid mechanics, 2020, 286, 104444 (Year: 2020).*

Habibi, Sara, et al., "Wettability alteration analysis of smart water/ novel functionalized nanocomposites for enhanced pil recovery", Petroleum Science, The Authors, vol. 17, Apr. 2020, pp. 1318-1328 (11 pages).

Hua, Zhao, et al., "Effect of injection brine composition on wettability and oil recovery in sandstone reservoirs", Fuel, ScienceDirect, Elsevier Ltd., vol. 182, Jun. 2016, pp. 687-695 (9 pages).

* cited by examiner

DYNAMIC IN-SITU MEASUREMENT OF CALCIUM ION CONCENTRATION IN POROUS MEDIA EXPERIMENTS

BACKGROUND

In the field of oil and gas, waterflooding is a process to increase production from hydrocarbon-bearing reservoirs. A waterflooding process injects water into a hydrocarbon-producing reservoir. The hydrocarbons within the reservoir is displaced by the water and is pushed toward an adjacent production well. The displaced hydrocarbons are collected and produced.

Waterflooding fluid is often based on a high salinity fluid, such as seawater or brine. Recent research studies have shown that reducing the salinity of water in waterflooding may have a favorable impact on wettability. Wettability of the reservoir rock or mineral is strongly correlated to permeability and general waterflooding behavior. A favorable impact on wettability may result in increased oil recovery.

Coreflooding is a laboratory test that introduces fluid, such as water, into a rock sample to measure interactions between the fluid and the rock. The rock sample used in coreflooding may come from a reservoir, for example, to measure feasibility of a waterflooding process. The lab equipment used for a coreflooding test is a general coreflood apparatus and may be found in in a petroleum research lab.

SUMMARY

This Summary is provided to introduce a selection of concepts that are further described below in the Detailed Description. This Summary is not intended to identify key or essential features of the claimed subject matter, nor is it intended to be used as an aid in limiting the scope of the claimed subject matter.

In one aspect, a coreflood apparatus is provided that may comprise a housing including an inlet end and an outlet end; an inlet coupled to the housing and positioned at the inlet end; an outlet coupled to the housing and positioned at the outlet end; and two chambers positioned within the housing between the inlet and the outlet, configured to retain porous media. The two chambers may be in series along a fluid flow pathway through the coreflood apparatus, and the two chambers may prevent fluid bypass around the porous media. The coreflood apparatus may further comprise a partition coupled to an inner surface of the housing and positioned between the two chambers; and a sensor mounting location in the housing to define access via a sensor and to permit detection with the sensor. The coreflood apparatus may be configured to pass fluid through the inlet and through the housing.

In another aspect, a method is provided that may comprise introducing a fluid into a coreflood apparatus at an inlet. The coreflood apparatus may comprise a housing including an inlet end and an outlet end. The inlet may be coupled to the housing and positioned at the inlet end. The coreflood apparatus may comprise an outlet coupled to the housing and positioned at the outlet end. The coreflood apparatus may further comprise two chambers positioned within the housing between the inlet and the outlet, configured to retain porous media, where the two chambers are in series along a fluid flow pathway through the coreflood apparatus, and where the two chambers prevent fluid bypass around the porous media. The coreflood apparatus may comprise a partition coupled to an inner surface of the housing and positioned between the two chambers, and a sensor mounting location in the housing to define access via a sensor. The coreflood apparatus is configured to introduce the fluid at the inlet and pass the fluid through the housing. The method may include introducing the fluid at the inlet, allowing the fluid to pass from the inlet to the sensor mounting location.

In another aspect, a coreflood system is provided that may comprise a housing including an inlet end and an outlet end; an inlet coupled to the housing and positioned at the inlet end; an outlet coupled to the housing and positioned at the outlet end; and two chambers positioned within the housing between the inlet and the outlet, configured to retain porous media. The two chambers may be in series along a fluid flow pathway through the coreflood system, and the two chambers prevent fluid bypass around the porous media. The coreflood system may further comprise a partition coupled to an inner surface of the housing and positioned between the inlet and the outlet, and a calcium ion sensor and a sensor mounting location in the housing to define access via the calcium ion sensor. The calcium ion sensor may be coupled to the sensor mounting location with access to the fluid flow pathway. The coreflood system may further comprise a data processing device. The coreflood system may be configured to pass fluid through the inlet and through the housing.

In yet another aspect, a method is provided that may comprise introducing a fluid into a coreflood system at an inlet. The coreflood system may comprise a housing including an inlet end and an outlet end, where the inlet may be coupled to the housing and positioned at the inlet end, an outlet coupled to the housing and positioned at the outlet end, and two chambers positioned within the housing between the inlet and the outlet, configured to retain porous media. The two chambers may be in series along a fluid flow pathway through the coreflood system, and the two chambers may prevent fluid bypass around the porous media. The coreflood system may comprise a partition coupled to an inner surface of the housing and positioned between the two chambers, a sensor mounting location in the housing to define access via a calcium ion sensor, and a calcium ion sensor coupled to the sensor mounting location with access to the fluid flow pathway. The coreflood system may further comprise a data processing device coupled to the calcium ion sensor that determines, using calcium ion data from the calcium ion sensor, a calcium ion concentration within the fluid. The coreflood system may be configured to introduce the fluid at the inlet and pass the fluid through the housing, where introducing the fluid at the inlet allows the fluid to pass from the inlet to the calcium ion sensor. The method may further comprise detecting calcium ions in the fluid with the calcium ion sensor and allowing the calcium ion sensor to pass the calcium ion data to the data processing device. Other aspects and advantages of the claimed subject matter will be apparent from the following Detailed Description and the appended Claims.

BRIEF DESCRIPTION OF DRAWINGS

In the figures, a "'" refers to the same element in a different state, that is, all other aspects of the elements are the same but for a modification in operation. In the figures, like numbers may refer to like elements.

DETAILED DESCRIPTION

In one or more embodiments, a coreflood apparatus has an inlet, an outlet, two or more chambers therebetween, and a partition between each pair of chambers. Such an apparatus may be used to retain two or more core samples in an apparatus—each sample in its own chamber—while fluid may be introduced at the inlet. As fluid flows through porous media, such as core samples, the coreflood apparatus may be used to detect changes in the fluid passing from porous media and therefore determine changes to porous media.

Data collected from a coreflooding experiment using a coreflood apparatus may be useful to analyze damage to the core sample caused by the introduced fluid. For example, analytical data can be useful in determining improvements in a large-scale waterflooding process.

High salinity waterflooding fluids may have high concentrations of divalent cations, such as calcium and magnesium, compared to low salinity fluids, like fresh water. In addition, divalent cations, such as calcium, are present in carbonate rocks and other reservoir rocks. These divalent cations may play a role in interactions between fluid and rock. Altering the concentration of divalent cations in water may result in rock wettability alteration during waterflooding.

In one or more embodiments, a coreflood apparatus, a coreflood system, and a method of use are provided. One or more embodiments may be used to determine in-situ concentrations of calcium ions during coreflooding.

Determining calcium ion concentration at different positions along the fluid flow pathway of the coreflood apparatus, such as before, between, or after one or more core samples, may help to predict physiochemical interaction between different fluid and rock combinations.

Coreflood Apparatus

Figure 1A:
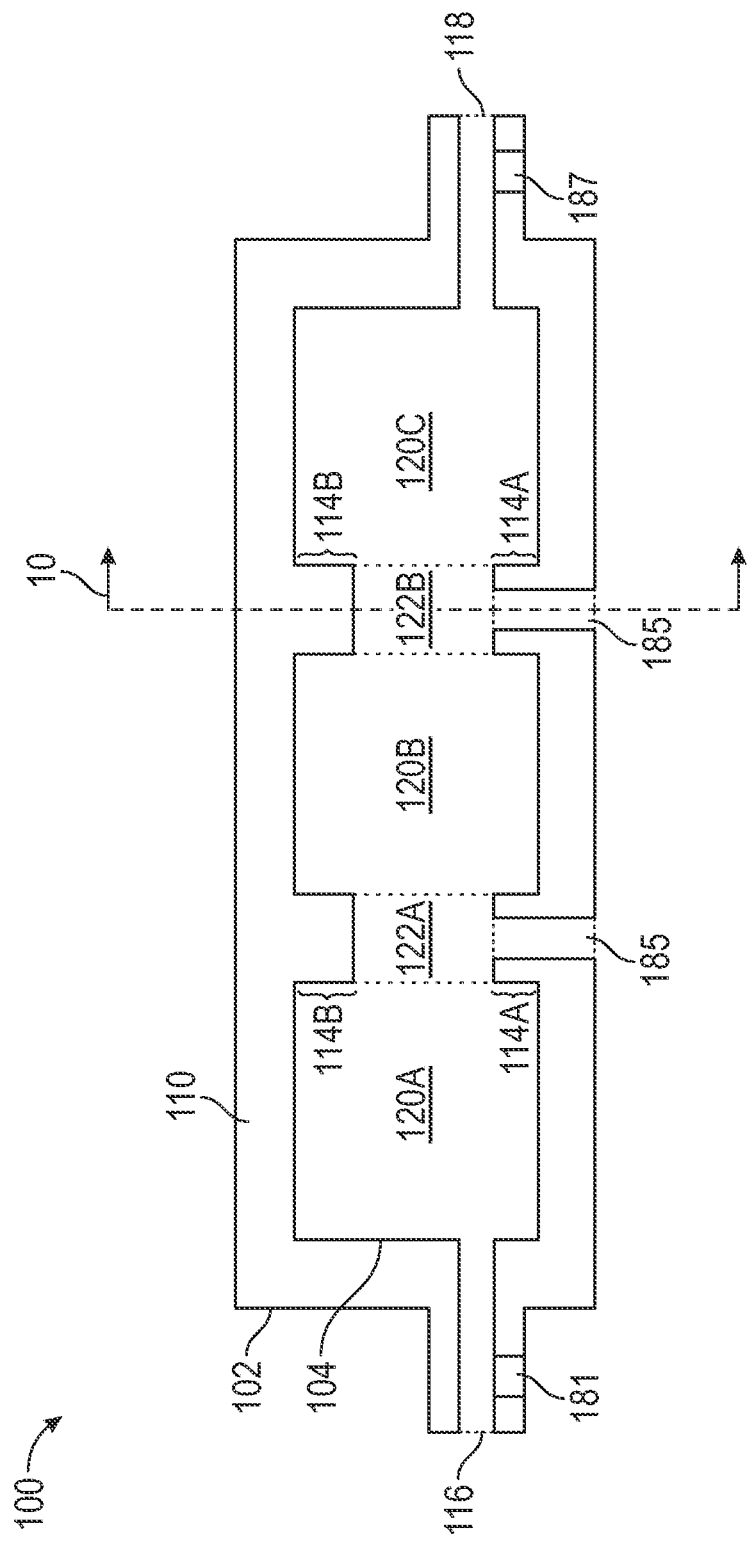
FIG. 1A shows a cross-sectional view of a coreflood apparatus, according to one or more embodiments.

FIG. 1A depicts a cross-sectional view of the coreflood apparatus 100 of one or more embodiments. The cross-sectional view shows the coreflood apparatus 100 and the general fluid flow pathway from inlet end (left) to outlet end (right). The coreflood apparatus 100 includes a housing 110. The housing 110 has an outer surface 102 and an inner surface 104. The inner surface 104 of the housing 110 defines the interior of the coreflood apparatus 100, including the chambers. FIG. 1A shows inlet chamber 120A, middle chamber 120B, and outlet chamber 120C. An inlet 116 is defined by the housing 110 at the inlet end; an outlet 118 is defined by the housing 110 at the outlet end. The coreflood apparatus 100 is configured such that a fluid may be introduced through the inlet 116, traverse the interior of the housing 110, and pass from the outlet 118.

The inner surface 104 defines an open space within the housing 110. Between the inlet 116 and the outlet 118, a plurality of chambers are defined within the housing 110. In FIG. 1A, three chambers are shown. Inlet chamber 120A, middle chamber 120B, and outlet chamber 120C are in series and in fluid communication with one another along the fluid flow pathway. The inlet 116 is configured to pass fluid to the inlet chamber 120A. The outlet 118 is configured to receive fluid from the outlet chamber 120C.

The inner surface 104 also defines partitions within the housing. A partition is positioned between two chambers in series (each of two chambers) and in part defines the configuration of a chamber and a partition gap. For example, there is a partition positioned in between inlet chamber 120A and middle chamber 120B, which defines a partition gap 122A. There is another partition positioned in between middle chamber 120B and outlet chamber 120C, forming a partition gap 122B. A partition is configured to separate the chambers. Thus, the partition defines both a part of each chamber and a partition gap that exists between and is in fluid connectivity with each chamber.

As shown in FIG. 1A, the partition may have two parts: a portion of the partition with a sensor mounting location 114A and another portion of the partition without sensor mounting location 114B.

The configuration of the housing of the coreflood apparatus provides for at least one partition having a sensor mounting location. The sensor mounting location may define access through the housing for a calcium ion sensor and permit detection of calcium ions in a fluid flowing through the coreflood apparatus with the calcium ion sensor. Meaning, the configuration of the partition with the sensor mounting location may define an orifice or void, such as a hole or a conduit, to house a sensor, to be described. For example, the sensor mounting location may include threads, a poppet, a grommet, a clamp, an O-ring, or other suitable configuration to retain a sensor. When a sensor is not included at the sensor mounting location, the sensor mounting location may be blocked off to prevent fluid loss or gas exchange, for example, blocked off with a plug.

The housing of the coreflood apparatus may be configured such that there are more than one sensor mounting location along the fluid flow pathway of the coreflood apparatus. In some instances, the housing of the coreflood apparatus may be configured such that there is a sensor mounting location within a partition. In some instances, the housing of the coreflood apparatus may be configured such that there is a sensor mounting location proximate to the fluid inlet. In some instances, the housing of the coreflood apparatus may be configured such that there is a sensor mounting location proximate to the fluid outlet.

In FIG. 1A, an inlet sensor mounting location 181 is positioned upstream of inlet chamber 120A. A middle sensor mounting location 185 is positioned between chambers. For example, two middle sensor mounting locations are shown in FIG. 1A: between inlet chamber 120A and middle chamber 120B, and between middle chamber 120B and outlet chamber 120C. An outlet sensor mounting location 187 is positioned downstream of outlet chamber 120C.

Figure 1B:
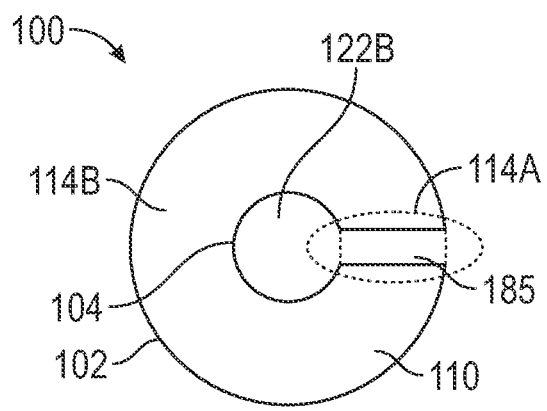
FIG. 1B shows a cutaway cross-sectional view of a coreflood apparatus, according to one or more embodiments.

In FIG. 1A, bifurcation line 10 defines a cross-sectional view from upstream to downstream, to be described. FIG. 1B depicts a cross-sectional view of a coreflood apparatus 100 according to one or more embodiments based upon bifurcation line 10 of FIG. 1A. In FIG. 1B, the housing 110, the outer surface 102, the inner surface 104 define a thick circle-like shape as the partition and a small circle as partition gap 122B. A portion of the partition with sensor mounting location 114A protrudes into the partition gap 122B. The middle sensor mounting location 185 defined by the portion of the partition with sensor mounting location 114A provides fluid communication with the fluid that would flow through partition gap 122B. The remainder of partition is not associated with defining a sensor mounting location, so is demarcated as a portion of the partition without sensor mounting location 114B.

Figure 1C:
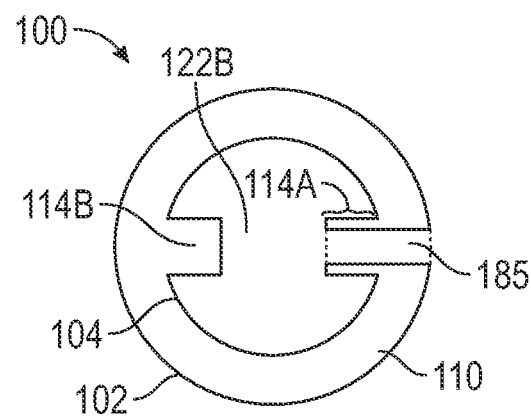
FIG. 1C shows a cutaway cross-sectional view of a coreflood apparatus, according to one or more embodiments.

FIG. 1C depicts a cross-sectional view of the coreflood apparatus 100 according to one or more embodiments based upon bifurcation line 10 of FIG. 1A. In FIG. 1C, the housing 110, the outer surface 102, the inner surface 104 define a thin circle-like shape as the partition and a large circle as partition gap 122B. A portion of the partition with sensor mounting location 114A protrudes into the partition gap 122B. The middle sensor mounting location 185 defined by the portion of the partition with sensor mounting location 114A provides fluid communication with the fluid that would flow through partition gap 122B. A second portion of the partition protrudes into the partition gap 122B. However, this second portion of the partition is not associated with defining a sensor mounting location, so is demarcated as a portion of the partition without sensor mounting location 114B.

Figure 1D:
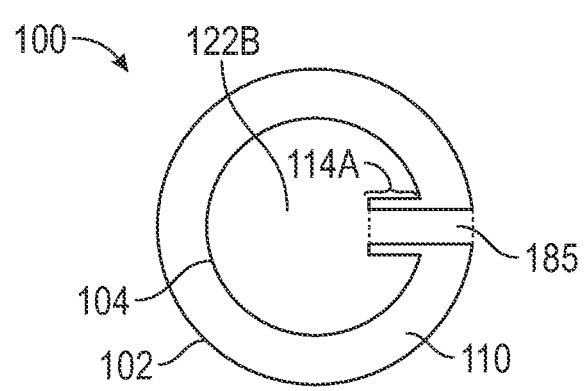
FIG. 1D shows a cutaway cross-sectional view of a coreflood apparatus, according to one or more embodiments.

FIG. 1D depicts a cross-sectional view of a coreflood apparatus 100 according to one or more embodiments based upon bifurcation line 10 of FIG. 1A. In FIG. 1D, the housing 110, the outer surface 102, the inner surface 104 define a thin circle-like shape as the partition and a large circle as partition gap 122B. The portion of the partition with sensor mounting location 114A protrudes into the partition gap 122B. The middle sensor mounting location 185 defined by the portion of the partition with sensor mounting location 114A provides fluid communication with the fluid that would flow through partition gap 122B. FIG. 1D is different from FIG. 1A in that the partition defines the middle sensor mounting location. That is, in FIG. 1D a portion of the partition without the sensor mounting location 114B is absent.

Figure 1E:
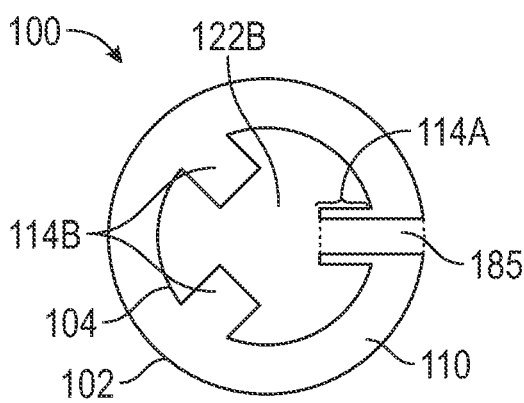
FIG. 1E shows a cutaway cross-sectional view of a coreflood apparatus, according to one or more embodiments.

FIG. 1E depicts a cross-sectional view of the coreflood apparatus 100 according to one or more embodiments based upon bifurcation line 10 of FIG. 1A. In FIG. 1E, the housing 110, the outer surface 102, the inner surface 104 define a thin square-like shape as the partition and a large square as partition gap 122B. The portion of the partition with sensor mounting location 114A protrudes into the partition gap 122B. The middle sensor mounting location 185 defined by the portion of the partition with sensor mounting location 114A provides fluid communication with the fluid that would flow through partition gap 122B. FIG. 1E is different from FIG. 1A in that there are two partitions that do not define the middle sensor mounting location. That is, there are two partitions (portion of partition without sensor mounting location 114B) that protrude into partition gap 122B.

In one or more embodiments, a coreflood apparatus is provided that includes a housing, such as a coreholder, with an inlet and an outlet and a partition therebetween. The partition separates the housing into separate chambers. The chambers are positioned in series and are configured to retain porous media, such as a core sample. A partition is also configured to retain porous media and to separate a sample of porous media from another sample. The partition or the housing itself may be configured to retain a sensor. The chambers and the partitions are configured such that when a core sample is present in the coreflood apparatus the introduced fluid traverses the core sample.

The housing of the apparatus includes walls that may define an inner surface and an outer surface of the housing. The housing may be configured to allow a fluid to traverse the interior of the housing. The inner surface of the housing defines the open space, or void, within the housing, including, but not limited to, an inlet, an outlet, a plurality of chambers, and at least one partition gap. There may be more than one inlet, such as a water inlet (to introduce aqueous solutions) and an oil inlet (to introduce oleaginous solutions). When the housing includes more than one inlet, the location of the more than one inlet is next to each other or just below the inlet in a parallel position (such as an inlet shown in the figures). In one or more embodiments, the housing is configured to retain porous media. When the porous media is a core sample, the housing may be called a coreholder.

The walls of the housing may be a suitable thickness that allows porous media retention and fluid flow according to one or more embodiments. The wall thickness of the housing depends on, for example, pressure rating and pipe size, and the wall thickness may be from about 0.1 inch (0.25 centimeter, cm) to about 1 inch (2.5 cm), such as from about 0.343 inch (0.87 cm) to about 0.531 inch (1.35 cm). The walls of the housing may be a material such as stainless steel, aluminum, or an alloy such as nickel-molybdenum alloy. The housing is configured to withstand a fluid pressure of up to 4,500 pounds per square inch (psi) (31 megapascal, MPa) and a temperature of up to 250° F. (121° C.).

In one or more embodiments, the coreflood apparatus includes a plurality of chambers, including, but not limited to, two chambers or more than two chambers. The coreflood apparatus may include two or more chambers, such as three or more, four or more, or five or more chambers. The chambers are positioned within the housing between the inlet and the outlet. A chamber is defined by an interior "open" space within the housing, where a chamber is separated from an adjacent chamber by a partition. A partition creates a "partition" space (gap or void) that separates two chambers; however, there is fluid connectivity between the two separate chambers. The gap or void between adjacent chambers defined by the partition may be called a partition gap. When a chamber is coupled to an inlet, it may be called an inlet chamber. When a chamber is coupled to an outlet, it may be called an outlet chamber. When a chamber is between an inlet chamber and an outlet chamber, it may be called a middle chamber.

When two middle chambers are included, they may be referred to as upstream middle chamber and downstream middle chamber. When more than two middle chambers are included, the upstream-most chamber may be referred to as the first middle chamber, labelled in series (second, third, and so on) to the final middle chamber (which would be the downstream-most middle chamber).

In one or more embodiments, the chambers are configured to retain porous media. For example, when the porous media is a core sample, a chamber retains the core sample. In one or more embodiments, the chambers are fluidly connected in series along a fluid flow pathway through the coreflood apparatus. The chambers are configured to prevent fluid bypass around the core sample contained within.

The size of a chamber may vary from one chamber to another depending on a variety of features and design choices, such as the size and thickness of the housing, and size and thickness of the partition(s). In one example, the chamber is configured to retain porous media of up to about 20 inches (about 51 centimeters) in length and up to about 1.5 inches (about 3.81 centimeters) in diameter. The chamber may include a sleeve, where the sleeve mimics the overburden pressure underground.

In one or more embodiments, the coreflood apparatus includes one or more partition. In one or more embodiments, the coreflood apparatus includes more than one partition, such as two or more partitions, three or more partitions, or four or more partitions. A partition is positioned between two adjacent chambers, separating the chambers physically from one another and through space (partition gap). A partition is configured in such a way to allow fluid to flow between adjacent chambers through the partition gap. The partition is coupled or connected to the housing. The partition may be affixed to the inner surface of the housing or may be integral to the housing walls. The partition extends inward from the inner surface of the housing. A partition is made of aluminum.

The size of a partition may vary. The length of the partition, measured from the inner surface of the housing to the tip of the partition, may protrude into the partition gap up to about 3 inches (7.62 cm). For example, the length of the partition may be from 0.1 to 3 inches (0.25 to 7.62 cm), such as from about 0.1 to 2 inches (0.25 to 5.08 cm), 0.5 to 3 inches (1.27 cm to 7.62 cm), 1 to 3 inches (2.54 to 7.62 cm), and 1 to 2 inches (2.54 to 5.08 cm). The lower limit height of the partition is about 0.1 inches, so long as the partition is configured to retain the porous media and define the dimensions of the chamber (along with the inner surface of the housing). The height of the partition may range from about 0.1 to 3 inches, such as from about 0.1 to 2 inches, 0.5 to 3 inches, 0.5 to 2 inches, 1 to 3 inches, or 1 to 2 inches. The width of the partition may be up to about 10 inches. The lower limit width of the partition is about 0.1 inches, so long as the partition is configured to retain the porous media and define the dimensions of the chamber (along with the inner surface of the housing). For example, the width of the partition may be from 0.1 to 3 inches, such as from about 0.1 to 2 inches, 0.5 to 3 inches, 0.5 to 2 inches, 1 to 3 inches, or 1 to 2 inches.

Method of Using Coreflood Apparatus

Figure 4:
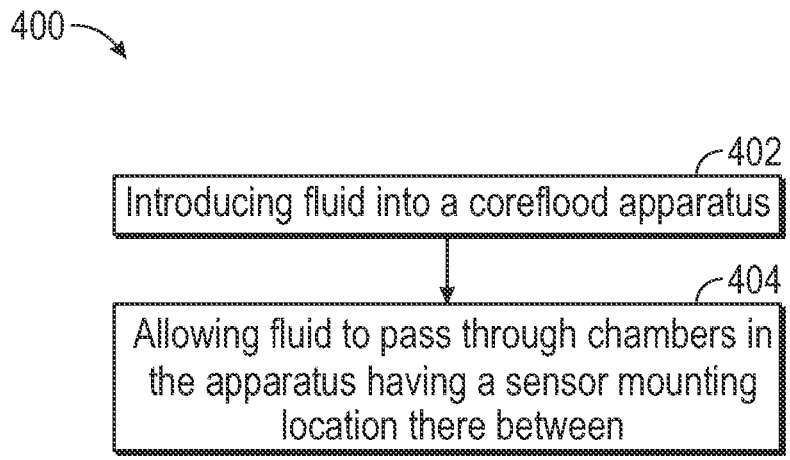
FIG. 4 shows elements of a method for introducing fluid into a coreflood apparatus, according to one or more embodiments.

FIG. 4 shows a method 400 according to one or more embodiments. The method 400 includes introducing fluid into a coreflood apparatus 402 and allowing fluid to pass through chambers in the coreflood apparatus 404, where the system includes a sensor mounting location between the chambers.

A method is provided that includes operating the system such that a fluid is introduced into the coreflood apparatus. The method of one or more embodiments may include operating the apparatus such that fluid passes through the chambers and partition gaps of the coreflood apparatus such that the fluid contacts a sensor mounting location. In some embodiments, the system may be operated such that the fluid flow within the coreflood system may be dynamic, such as by adjusting the composition, flow rate, pressure, or temperature of the introduced fluid.

The method may include introducing a porous media into one or more chamber. In one or more embodiments, the method may include introducing fluid into the coreflood apparatus at an inlet and allowing the fluid to pass from the inlet to a sensor mounting location. The method may include allowing the fluid to pass through porous media, to multiple sensor mounting locations, or to the outlet.

In one or more embodiments, the method includes adjusting a flow rate, a pressure, or a temperature of the fluid. Such fluid adjustments occur at or upstream of the inlet. The flow rate of the fluid may be in a range of from about 0.5 to about 5 centimeter cubed per minute ($cm^3/min$). The fluid pressure may be in a range up to an overburden pressure of from about 450 pounds per square inch (psi) (about 3.1 MPa) to about 2500 psi (about 17.2 MPa). The coreflood system may withstand a back pressure in the range of from about 200 psi (about 1.3 MPa) to about 500 psi (about 3.5 MPa). A fluid pressure may be from about 3,000 psi (about 20.6 MPa) to about 3,500 psi (24.1 MPa). A fluid temperature may be from about room temperature, about 77° F. (about 25° C.), to about 250° F. (about 121° C.).

The method of one or more embodiments may continue for up to a month. For example, at a low flow rate such as from about 0.1 $cm^3/min$ to about 4 $cm^3/min$, the experiment can be run for a time period of up to 1 month, such as from 3 days to a month, from 3 days to 4 weeks, from 3 days to 3 weeks, from 3 days to 2 weeks, or from 3 days to 1 week.

Coreflood System Including Calcium Ion Sensors

Figure 2:
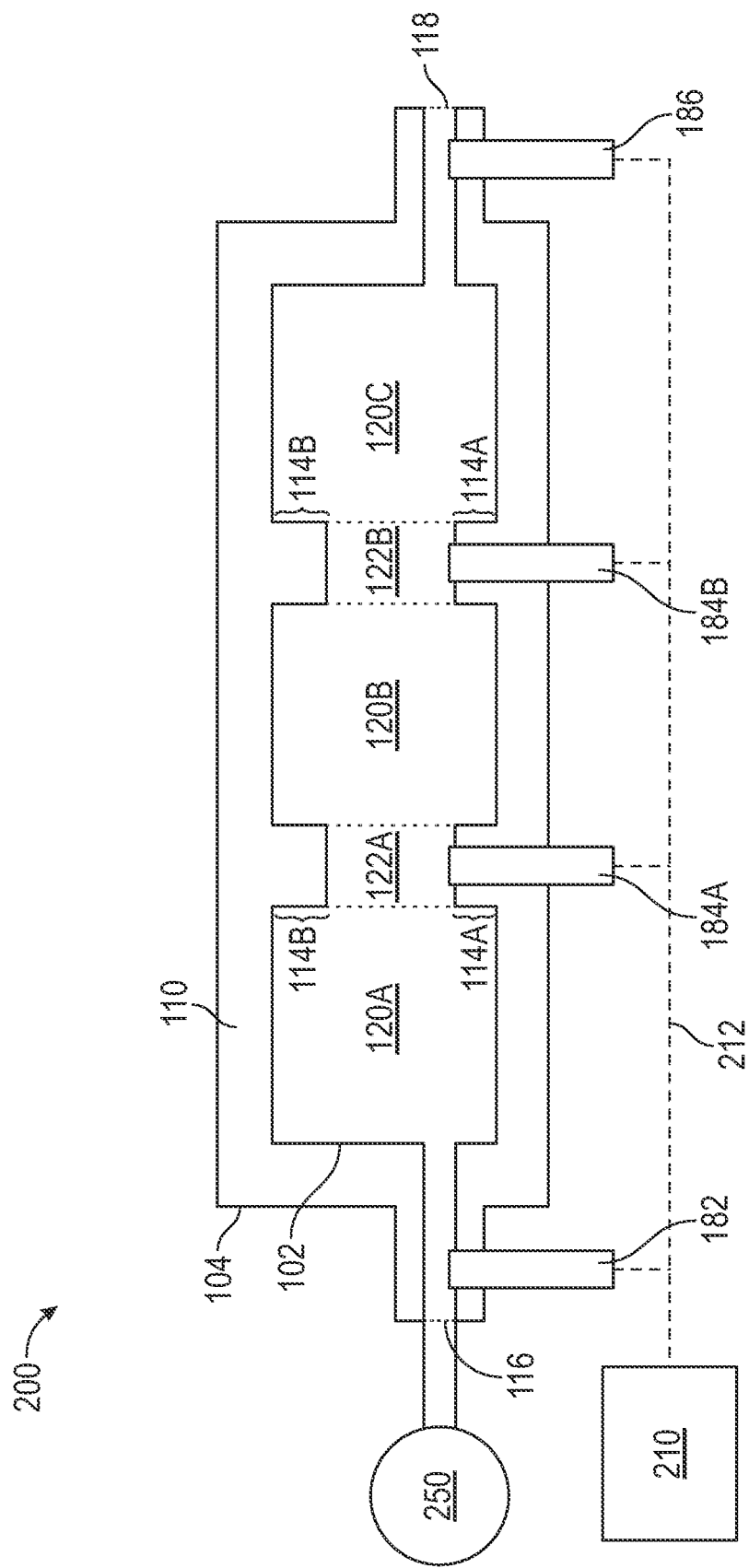
FIG. 2 shows a coreflood system with calcium ion sensors, according to one or more embodiments.

FIG. 2 shows a coreflood system 200 according to one or more embodiments. The coreflood system 200 includes a coreflood apparatus of one or more embodiments. The coreflood system also includes several calcium ion sensors, where a calcium ion sensor is coupled to the coreflood apparatus at a sensor mounting location (in FIG. 2, each sensor is positioned within a sensor mounting location). FIG. 2 shows an inlet calcium ion sensor 182, a middle calcium ion sensor (two are shown in FIG. 2, upstream middle calcium ion sensor 184A and downstream middle calcium ion sensor 184B), and an outlet calcium ion sensor 186. Each calcium ion sensor is configured to contact the fluid contained within the housing 110 and to detect calcium ions in the fluid. For example, the inlet calcium ion sensor 182 may detect calcium ions in the fluid at the inlet 116. The upstream middle calcium ion sensor 184A may detect calcium ions in the fluid in the partition gap 122A. The downstream middle calcium ion sensor 184B may detect calcium ions in the fluid in the partition gap 122B. The outlet calcium ion sensor 186 may detect calcium ions in the fluid in the outlet 118.

Each calcium ion sensor is also in data communication (calcium ion data) with data processing device 210. Each calcium ion sensor may be coupled to the data processing device either physically or wirelessly. For example, in FIG. 2, the calcium ion sensors (182, 184A, 184B, and 186) are coupled to a data processing device 210 utilizing a data conduit 212 (dotted line). The data processing device is configured to receive a data signal (calcium ion data) and to determine calcium ion concentration within the fluid.

The coreflood system 200 may include a pump 250. The pump shown in FIG. 2 is fluidly coupled or connected to the coreflood apparatus and positioned upstream of the inlet 116.

Figure 3:
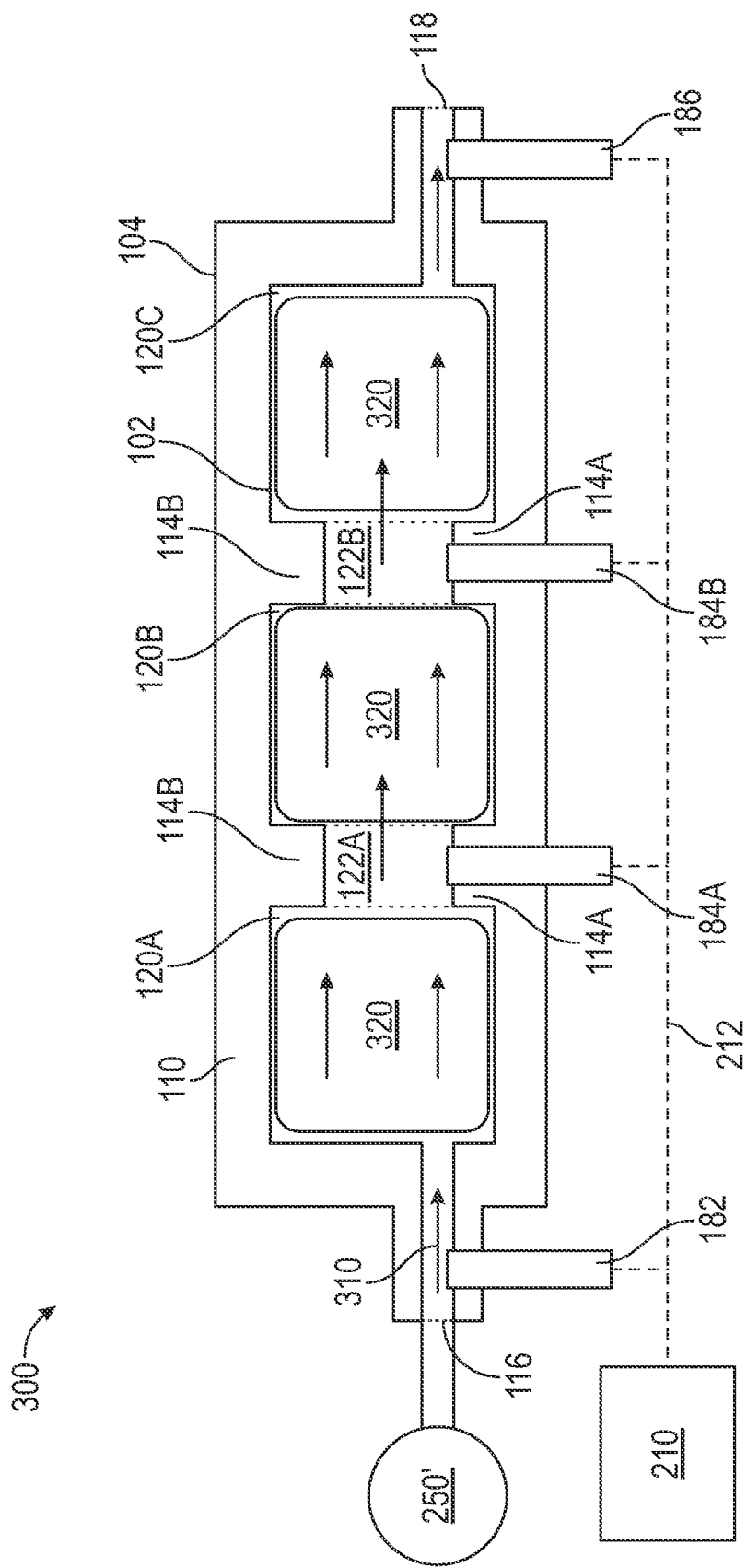
FIG. 3 shows a coreflood system in an active state including porous media and showing direction of fluid flow, according to one or more embodiments.

FIG. 3 shows a coreflood system 300 in an active state, according to one or more embodiments. Porous media 320 is shown in inlet chamber 120A, middle chamber 120B, and outlet chamber 120C. The pump 250' is in an active state, passing fluid to the inlet 116. Fluid 310 is flowing (arrows) through the coreflood system 300. The fluid 310 passes into inlet chamber 120A, middle chamber 120B, and outlet chamber 120C in succession and the porous media 320 contained in the chambers. As shown in FIG. 3, fluid 310 may flow from the outlet 118 and the coreflood system 300 itself. Although not shown, a collection apparatus or vessel may be present downstream of the outlet 118 to collect the fluid 310.

In FIG. 3, the calcium ion sensor(s) may detect calcium ion data in the fluid in contact with the tip of the sensor(s). For example, in inlet 116 the inlet calcium ion sensor 182 may detect the calcium ion concertation of the fluid 310 just as it is introduced into the coreflood system. In partition gap 122A, the upstream middle calcium ion sensor 184A may detect the calcium ion concertation of the fluid 310 just as it passes from the upstream core sample (porous media 320) in inlet chamber 120A. In partition gap 122B, the downstream middle calcium ion sensor 184B may detect the calcium ion concertation of the fluid 310 just as it passes from the middle core sample (porous media 320) in middle chamber 120B. In outlet 118, the outlet calcium ion sensor 186 may detect the calcium ion concertation of the fluid 310 just as it passes from the downstream core sample (porous media 320) in outlet chamber 120C and as it passes from the coreflood system. Each calcium ion sensor is configured to communicate a signal associated with the calcium ions detected in the fluid as data to the data processing device 210. The data processing device 210 may determine calcium ion concentration from the received data. The data processing device 210 may determine changes or differences in calcium ion concentration at various positions along the fluid flow pathway of the coreflood apparatus.

In one or more embodiments, a coreflood system is provided that includes the coreflood apparatus, a calcium ion sensor, and a data processing device. The coreflood system may include one or more calcium ion sensors, such as two or more, or three or more calcium ion sensors. A calcium ion sensor is selective for detecting calcium ions in a fluid. The one or more sensors may be positioned anywhere along the fluid flow pathway within the housing, to be described. Multiple calcium ion sensors may be positioned such that they contact the fluid along the fluid flow pathway within the housing of the coreflood apparatus. In this way, the coreflood system is configured to detect calcium ions with the calcium ion sensors and to determine calcium ion concentration with the data processing device.

When a plurality of calcium ion sensors are included in a coreflood system of one or more embodiments, they may be positioned in series along a given fluid flow pathway. Calcium ion sensors positioned in series allow calcium ion data to be detected at different positions in a coreflood system, such as at an inlet, between chambers, and at an outlet.

In some instances, a calcium ion sensor may be included at a sensor mounting location. In other instances, there may be less calcium ion sensors than the total number of sensor mounting locations. As a non-limiting example, there may be two calcium ion sensors and four sensor mounting locations.

An inlet calcium ion sensor may be positioned in a sensor mounting location within the housing upstream of the chambers. An inlet calcium ion sensor may be positioned in an fluid line upstream of the housing. There may be more than one inlet calcium ion sensor.

An outlet calcium ion sensor may be positioned within the housing downstream of the chambers. An outlet calcium ion sensor may be positioned in an effluent line downstream of the housing. There may be more than one outlet calcium ion sensor.

A middle calcium ion sensor may be positioned at a location between two chambers. There may be one or more middle calcium ion sensors.

A calcium ion sensor includes a calcium ion detector portion. The detector portion is configured to be in fluid communication with fluid. The calcium ion sensor is configured to detect calcium ions within the fluid. For example, as fluid passes over a calcium ion sensor at the detector portion, the detector portion intermingles with calcium ions, and transmit the response into a data signal (calcium ion data). The calcium ion sensor may detect calcium ions continuously, intermittently, in a pulse-width manner, or a combination thereof.

The type of calcium ion sensor is not particularly limited. Suitable examples of a calcium ion sensor include, but are not limited to, an amperometric sensor, such as a flow-through sensor with an Ag/AgCl reference electrode, a potentiometric sensor, such as an all-solid-state potentiometric sensor, an impedimetric sensor, or a voltage sensor. Examples of calcium ion sensors include a calcium combination ion selective electrode available from HACH® (Loveland, Colorado, USA) and a combined calcium ion-selective electrode from Metrohm AG® (Herisau, Switzerland). A reference solution, such as a KCl reference solution, may be used with a calcium ion sensor of one or more embodiments. For example, a reference solution for calibration purposes may be added before a coreflooding experiment as would be appreciated by one of ordinary skill in the art.

An example of an all-solid-state electrode may include, for example, an electrode with an electro-active material that is deposited on the electrode, such as graphene or carbon nanotubes. An electrode in an all-solid-state electrode may be, for example, an integrated calcium ion potentiometric strip, such as a conductive carbon ink-based ceramic substrate. In one or more embodiments, a calcium ion sensor includes a carbon electrode. In one or more embodiments, the carbon electrode is an all-solid-state electrode.

A calcium ion sensor may have a detection limit for calcium ions within a fluid, depending on the type of the sensor used. For example, the calcium ion sensor may have a calcium ion concentration detection limit such as from about 0.5 micromolar ($\mu M$) to about $1\times10^6$ $\mu M$. In an all-solid-state potentiometric sensor, the calcium ion detection limit may be in a range of from about 1 $\mu M$ to about $10\times10^4$ $\mu M$.

Other examples of calcium ion sensing may include, but are not limited to, mass spectrometry, optical emission spectrometry, atomic absorption, and titration (where titration is not limited to visible light analysis), enzyme assay, gas chromatography, ultraviolet-visible spectroscopy, fluorescence detection, nuclear magnetic resonance, or other suitable analytical laboratory equipment.

The calcium ion sensor may be configured to detect calcium ions in presence of organic media, such as organic solvent, oil, or other organic material. For example, an all-solid-state potentiometric sensor may detect calcium ions when the organic content of the aqueous solution is up to about 50 vol % (percent by volume) or less, such as up to 50 vol % organic media compared to the total volume of the fluid. A high concentration of organic media, such as about 50 vol % organic media compared to the total volume of the fluid, may age the calcium ion sensor to an extent that the detection limit of the sensor is reduced compared to without a high concentration of organic media.

The pump may have a variable flow rate, or a variable pressure, or both a variable flow rate and pressure. The pump flow rate may be a rate between from about 0.5 to about 5 cubic centimeters per minute ($cm^3$/min) (or milliliters per minute, mL/min). The pump pressure may produce a discharge pressure of up to 2500 pounds per square inch (psi) (about 17.3 megapascal, MPa). The pump may have an overburden pressure range of from 450 to 2500 psi (about 3 to 17.3 MPa). The pump may continue to operate with a back pressure in a range of up to about 500 psi (about 3.5 MPa)), such as from about 200 to about 500 psi (about 1.3 to about 3.5 MPa) back pressure.

Depending on the pressure and volume (flow rate), the system may be configured to pass fluid for up to one month, such as up to 3 weeks, 2 weeks, 1 week, 6 days, 5 days, 4 days, 3 days, 2 days, 1 day, or less than 1 day. A low flow rate, such as from 0.01 $cm^3$/min to 1 $cm^3$/min may be used for long-duration, such as greater than 5 days.

A data processing device is configured to receive a data signal (calcium ion data) from the calcium ion sensor and to determine calcium ion concentration of a fluid. The data processing device may also determine a change in calcium ion concentration of a fluid over time. The data processing device may include a computer processor. The data processing device may include a form of data processing with or without a computer processor, such as a potentiometer, an amperage meter, a voltage meter, a resistance meter, a multimeter, or other suitable form of data processing. The data processing device may include a receiver, including, but not limited to, a Wi-Fi, Bluetooth, or radio receiver.

The coreflood apparatus is configured to retain porous media within the chambers. The porous media may include, but is not limited to, an outcrop plug, a sand pack, a reservoir rock, or a combination thereof. The porous media may be a source of calcium ions. The porous media may be a single core sample that is cut into pieces, or multiple different core samples. Porous media is positioned in series along a given fluid flow pathway within a series of chambers of the coreflood apparatus or coreflood system. FIG. 3 shows an example with three samples of porous media positioned in series along a given fluid flow pathway.

The fluid may be an aqueous-based fluid. For example, the aqueous base of the fluid may include, but is not limited to, brine, seawater, freshwater, processed water, distilled water, alkaline water, reservoir water, a combination thereof, or other suitable types of water.

The fluid may be a source of calcium ions, meaning the fluid may include calcium ions. A fluid without calcium ions may be used. Multiple types of fluid (fluids having different compositions) may be introduced, either simultaneously, one after the other, or intermittently. Generally, water and saline water, petroleum, oil, and formation water may be used, and mixtures thereof. Gas or alternating a gas and a liquid may also be used, such as occurs in mimicking $CO_2$ enhanced oil recovery processes.

The aqueous base fluid may include up to 50 volume % (vol %) organic media. Organic media may include solvent, hydrocarbon, microorganisms, or intractable organic material.

One of ordinary skill in the art would appreciate variations of a coreflood apparatus and a coreflood system. For example, the coreflood apparatus or system may include an overpressure burst disk and a relief valve to protect the system against accidental over-pressure. The relief valve may be located in the housing. A syringe pump may be used to control the injection pressure or flow rate setting. A heating system may include a heating element or heating tape around the apparatus or the apparatus may be kept inside an industrial oven for heating.

Method of Using Coreflood System

Figure 5:
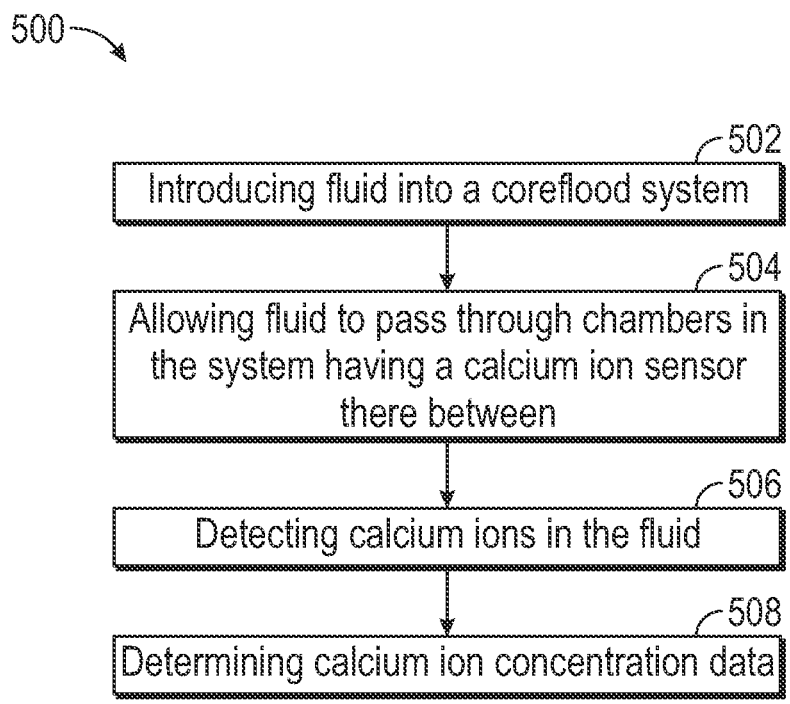
FIG. 5 shows elements of a method for determining calcium ion concentration in a fluid that is introduced into a coreflood system, according to one or more embodiments.

FIG. 5 shows a method 500 according to one or more embodiments. The method 500 shows introducing fluid into a coreflood system 502 and allowing fluid to pass through chambers in the coreflood system 504, where the system includes a calcium ion sensor between the chambers. The method 500 includes detecting calcium ions 506 in the fluid and determining calcium ion concentration data 508.

A method is provided that includes operating the system such that a fluid is introduced into the coreflood system, such as into the coreflood apparatus. The method may include operating the system such that calcium ion data is detected in the fluid flowing through the coreflood system, such as in portions of the coreflood apparatus. The method of one or more embodiments may include detection of calcium ions at one or more position along the coreflood system, such as in portions of the coreflood apparatus. The method may include operating the system such that the calcium ion concentration or the change in calcium ion concentration of the fluid within the coreflood system is determined, such as by using a data processing device. In some embodiments, the system may be operated such that the fluid flow within the coreflood system may be dynamic, such as by adjusting the composition, flow rate, pressure, or temperature of the introduced fluid.

The method may include introducing porous media into one or more chamber. In one or more embodiments, the method includes introducing fluid into the coreflood system at an inlet such that the fluid passes from the inlet to a calcium ion sensor. The method may include the fluid passing through porous media, interacting with multiple calcium ion sensors, or passing from the outlet.

In one or more embodiments, the method includes detecting calcium ions in the fluid with a calcium ion sensor. The method may include detecting calcium ions instantaneously, intermittently, or continuously over a period.

Calcium ions may be detected at different calcium ion sensors positioned in the coreflood system. For example, calcium ions may be detected in the coreflood system at the inlet, the middle, the outlet, or at a combination thereof.

For example, the method may include detecting calcium ions at an inlet calcium ion sensor as fluid is introduced into the coreflood system. As fluid passes through the chambers, the method may include detecting calcium ions at a middle calcium ion sensor (and so on, where the coreflood system includes multiple middle calcium ion sensors). As fluid passes from the outlet chamber, the method may include detecting calcium ions at an outlet calcium ion sensor. Once the data processing device receives the calcium ion data, the method includes determining a calcium ion concentration. The method may include determining a calcium ion concentration at two or more positions, such as the inlet, the middle, and the outlet. The method may include determining a change in calcium ion concentration at one or more position, such as a cumulative change in calcium ion concentration at a position in the coreflood system (in coreflood apparatus).

In one or more embodiments, the method may include adjusting a flow rate, a pressure, or a temperature of the fluid. Generally, such fluid adjustments occur at or upstream of the inlet. The flow rate of the fluid may be in a range of from about 0.5 to about 5 $cm^3$/min. The fluid pressure may be in a range up to an overburden pressure of from about 450 pounds per square inch (psi) to about 2500 psi. The coreflood system may withstand a back pressure in the range of from about 200 psi to about 500 psi. A fluid pressure (pore pressure) may be from about 3,000 psia to about 3,500 psia. A fluid temperature may be from about room temperature (about 77° F.) (about 25° C.) to about 250° F. (about 121° C.).

The method of one or more embodiments may continue for up to a month. For example, at a low flow rate such as from about 0.01 $cm^3$/min to about 1 $cm^3$/min, the experiment can be run for a time period of up to 1 month, such as from 3 days to a month, from 3 days to 4 weeks, from 3 days to 3 weeks, from 3 days to 2 weeks, or from 3 days to 1 week.

Advantages

One or more embodiments of the coreflood system and method of use allows calcium ion detection in-situ. Meaning, calcium ion concentration data is collected internally within a 'closed' system (within the housing). Internal and in-situ calcium ion detection may provide insight into reaction mechanisms and properties of fluid specific to instantaneous through-core calcium ion measurements.

For example, fluid chemistry may behave differently within a porous media, or between two different porous media because of different wetting conditions and rock mineralogy. It is believed that such measurements advantageously imitate fluid flow within reservoir, such as internal flow between and calcium ion concentration variation between porous media. Such measurements will help to understand the in-situ interactions between fluids and rock minerals.

In addition, the ability to analyze calcium ion data from within a 'closed' system prevents artifacts and impurities from being collected, leading to more accurate results. For example, detecting calcium ions of the fluid in-situ provides accurate results compared to collecting effluent fractions. For example, the coreflood system of one or more embodiments may be controlled such that $CO_2$ in the air does not dissolve into the fluid. Preventing $CO_2$ dissolution advantageously provides stable calcium ion data and accurate calcium ion concentration results, as compared to, for example, collecting effluent fractions outside of a coreflooding apparatus.

The coreflood system of one or more embodiments includes chambers in series. This allows for increased fluid exposure to porous media, depending on the length of the chambers, compared to a coreflood system that may include chambers in parallel.

Advantageously, in-situ detection of calcium ion data removes an extent of operator skill and labor time as compared to a conventional method, for example, effluent collection and analysis. The system and method of one or more embodiments overcomes uncertainties in determining calcium ion concentration to provide robust, reliable, and accurate measurements.

As a result, applying one or more embodiments of the method herein may accurately predict a water flooding process, providing advantageous data to optimize water-flooding in the field and increase oil recovery.

As used here and in the appended claims, the words "comprise," "has," and "include" and all grammatical variations thereof are each intended to have an open, non-limiting meaning that does not exclude additional elements or steps.

"Optionally" means that the subsequently described event or circumstances may or may not occur. The description includes instances where the event or circumstance occurs and instances where it does not occur.

When the word "approximately" or "about" are used, this term may mean that there can be a variance in value of up to ±10%, up to ±5%, up to ±2%, up to ±1%, up to ±0.5%, up to ±0.1%, up to ±0.01%, up to +10%, up to +5%, up to +2%, up to +1%, up to +0.5%, up to +0.1%, up to +0.01%, up to −10%, up to −5%, up to −2%, up to −1%, up to −0.5%, up to −0.1%, or up to −0.01%.

Ranges may be expressed as from about one particular value to about another particular value, inclusive. When such a range is expressed, it should be understood that another one or more embodiments is from the one particular value to the other particular value, along with all particular values and combinations thereof within the range.

Although only a few example embodiments have been described in detail, those skilled in the art will readily appreciate that many modifications are possible in the example embodiments without materially departing from this disclosure. All modifications of one or more disclosed embodiments are intended to be included within the scope of this disclosure as defined in the following claims. In the claims, means-plus-function clauses are intended to cover the structures previously described as performing the recited function and not only structural equivalents, but also equivalent structures. It is the express intention of the applicant not to invoke 35 U.S.C. § 112(f) for any limitations of any of the claims, except for those in which the claim expressly uses the words 'means for' together with an associated function.

While one or more embodiments of the present disclosure have been described with respect to a limited number of embodiments, those skilled in the art, having benefit of this disclosure, will appreciate that other embodiments can be devised, which do not depart from the scope of the disclosure. Accordingly, the scope of the disclosure should be limited only by the attached claims.

What is claimed:

1. A coreflood apparatus, comprising:
   a housing including an inlet end and an outlet end;
   an inlet coupled to the housing and positioned at the inlet end;
   an outlet coupled to the housing and positioned at the outlet end;
   two chambers positioned within the housing between the inlet and the outlet, each chamber retaining porous media,
      wherein the porous media has a length of up to 20 inches and a diameter of up to 1.5 inches,
      wherein the two chambers are in series along a fluid flow pathway through the coreflood apparatus, and
      wherein the two chambers prevent fluid bypass around the porous media;
   a partition, comprising a partition gap in the partition, coupled to an inner surface of the housing and positioned between the two chambers, wherein the fluid flow pathway is disposed through the partition gap;
      wherein the partition has a height of from 0.1 to 3 inches that protrudes from the inner surface of the housing inward, and wherein the partition has a width of from 1 to 3 inches; and
   a sensor mounting location in the housing to define access via a sensor and to permit detection with the sensor,
      wherein the coreflood apparatus is configured to pass fluid through the inlet and through the housing.

2. The coreflood apparatus of claim 1, wherein the sensor mounting location includes an inlet sensor mounting location, positioned upstream of the two chambers.

3. The coreflood apparatus of claim 1, wherein the sensor mounting location includes a middle sensor mounting location, positioned between the two chambers.

4. The coreflood apparatus of claim 1, wherein the sensor mounting location includes an outlet sensor mounting location, positioned downstream of the two chambers.

5. The coreflood apparatus of claim 1, wherein the sensor mounting location is within the partition, such that the partition is configured to retain sensors.

6. The coreflood apparatus of claim 1, wherein the partition is affixed to the inner surface of the housing or a part of walls of the housing at the inner surface.

7. The coreflood apparatus of claim 1, comprising more than two chambers.

8. The coreflood apparatus of claim 1, wherein the partition gap is circular.

9. A method, comprising:
introducing a fluid into a coreflood apparatus at an inlet, wherein the coreflood apparatus comprises:
a housing including an inlet end and an outlet end, wherein the inlet is coupled to the housing and positioned at the inlet end,
an outlet coupled to the housing and positioned at the outlet end,
two chambers positioned within the housing between the inlet and the outlet, each chamber retaining porous media,
wherein the porous media has a length of up to 20 inches and a diameter of up to 1.5 inches,
wherein the two chambers are in series along a fluid flow pathway through the coreflood apparatus, and
wherein the two chambers prevent fluid bypass around the porous media,
a partition, comprising a partition gap in the partition, coupled to an inner surface of the housing and positioned between the two chambers, wherein the fluid flow pathway is disposed through the partition gap,
wherein the partition has a height of from 0.1 to 3 inches that protrudes from the inner surface of the housing inward, and wherein the partition has a width of from about 1 to 3 inches,
a sensor mounting location in the housing to define access via a sensor,
wherein the coreflood apparatus is configured to introduce the fluid at the inlet and pass the fluid through the housing, and
wherein introducing the fluid at the inlet allows the fluid to pass from the inlet to the sensor mounting location.

10. A coreflood system, comprising:
a housing including an inlet end and an outlet end;
an inlet coupled to the housing and positioned at the inlet end;
an outlet coupled to the housing and positioned at the outlet end;
two chambers positioned within the housing between the inlet and the outlet, each chamber retaining porous media,
wherein the porous media has a length of up to 20 inches and a diameter of up to 1.5 inches,
wherein the two chambers are in series along a fluid flow pathway through the coreflood system, and
wherein the two chambers prevent fluid bypass around the porous media;
a partition, comprising a partition gap in the partition, coupled to an inner surface of the housing and positioned between the inlet and the outlet, wherein the fluid flow pathway is disposed through the partition gap;
wherein the partition has a height of from 0.1 to 3 inches that protrudes from the inner surface of the housing inward, and wherein the partition has a width of from 1 to 3 inches;
a calcium ion sensor and a sensor mounting location in the housing to define access via the calcium ion sensor, wherein the calcium ion sensor is coupled to the sensor mounting location with access to the fluid flow pathway; and
a data processing device,
wherein the coreflood system is configured to pass fluid through the inlet and through the housing.

11. The coreflood system of claim 10, wherein the sensor mounting location includes an inlet sensor mounting location, positioned upstream of the two chambers, and wherein the calcium ion sensor includes an inlet calcium ion sensor coupled to the inlet sensor mounting location.

12. The coreflood system of claim 10, wherein the sensor mounting location includes a middle sensor mounting location, positioned between the two chambers, and wherein the calcium ion sensor includes a middle calcium ion sensor coupled to the middle sensor mounting location.

13. The coreflood system of claim 10, wherein the sensor mounting location includes an outlet sensor mounting location, positioned downstream of the two chambers, and wherein the calcium ion sensor includes an outlet calcium ion sensor coupled to the outlet sensor mounting location.

14. The coreflood system of claim 10, wherein the calcium ion sensor includes a carbon electrode.

15. The coreflood system of claim 10, comprising more than two chambers.

16. A method, comprising:
introducing a fluid into a coreflood system at an inlet, wherein the coreflood system comprises:
a housing including an inlet end and an outlet end, wherein the inlet is coupled to the housing and positioned at the inlet end,
an outlet coupled to the housing and positioned at the outlet end,
two chambers positioned within the housing between the inlet and the outlet, each chamber retaining porous media,
wherein the porous media has a length of up to 20 inches and a diameter of up to 1.5 inches,
wherein the two chambers are in series along a fluid flow pathway through the coreflood system, and
wherein the two chambers prevent fluid bypass around the porous media,
a partition, comprising a partition gap in the partition, coupled to an inner surface of the housing and positioned between the two chambers, wherein the fluid flow pathway is disposed through the partition gap,
wherein the partition has a height of from 0.1 to 3 inches that protrudes from the inner surface of the housing inward, and wherein the partition has a width of from 1 to 3 inches,
a sensor mounting location in the housing to define access via a calcium ion sensor,
the calcium ion sensor coupled to the sensor mounting location with access to the fluid flow pathway, and
a data processing device coupled to the calcium ion sensor, and the data processing device is configured to determine, using calcium ion data from the calcium ion sensor, a calcium ion concentration within the fluid,
wherein the coreflood system is configured to introduce the fluid at the inlet and pass the fluid through the housing,
wherein introducing the fluid at the inlet allows the fluid to pass from the inlet to the calcium ion sensor, and
detecting calcium ions in the fluid with the calcium ion sensor and allowing the calcium ion sensor to pass the calcium ion data to the data processing device.

17. The method of claim 16, further comprising determining a change in the calcium ion concentration in the fluid with the data processing device, using the calcium ion data from the calcium ion sensor.

18. The method of claim 16, wherein the porous media is a core sample.

19. The method of claim 18, wherein the core sample is an outcrop plug, a sand pack, a reservoir rock, or a combination thereof.

20. The method of claim 16, wherein the fluid includes 50 vol % organic media compared to total volume of the fluid.

21. The method of claim 16, wherein the fluid comprises brine, saline, water, formation water, or a combination thereof.

22. The method of claim 16, further comprising adjusting a flow rate of the fluid in a range of from about 0.5 to about 5 cubic centimeters per minute.

23. The method of claim 16, further comprising adjusting fluid pressure in a range up to about 3,500 psia (24.1 MPa).

24. The method of claim 16, further comprising adjusting fluid temperature in a range of from about 77° F. (about 25° C.) to about 250° F. (about 121° C.).

25. The method of claim 16, wherein introducing the fluid occurs for a time period of up to 1 month.

\* \* \* \* \*